(12) United States Patent
Chida et al.

(10) Patent No.: US 7,082,849 B2
(45) Date of Patent: Aug. 1, 2006

(54) APPARATUS AND METHOD FOR EXTRACTING VOLATILE CONSTITUENTS

(75) Inventors: Masahiro Chida, Kanagawa (JP); Yukio Sone, Kanagawa (JP); Taro Yonezawa, Kanagawa (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 10/625,594

(22) Filed: Jul. 24, 2003

(65) Prior Publication Data

US 2004/0182180 A1 Sep. 23, 2004

Related U.S. Application Data

(63) Continuation of application No. PCT/JP02/00668, filed on Jan. 29, 2002.

(30) Foreign Application Priority Data

Feb. 7, 2001 (JP) ............................ 2001-030923

(51) Int. Cl.
- G01N 1/02 (2006.01)
- G01N 1/22 (2006.01)
- G01N 1/24 (2006.01)

(52) U.S. Cl. ........................ 73/864.52; 73/864.51; 73/863.81; 73/863.85; 73/863.86

(58) Field of Classification Search ............ 73/863.11, 73/863.41, 863.42, 863.81, 863.85, 863.86, 73/864–864.91

See application file for complete search history.

(56) References Cited

U.S. PATENT DOCUMENTS

| | | | | |
|---|---|---|---|---|
| 2,999,738 A | * | 9/1961 | Redon | 73/864.31 |
| 3,205,700 A | | 9/1965 | Lively et al. | 73/19.02 |
| 3,290,889 A | * | 12/1966 | Nii | 62/3.3 |
| 4,008,621 A | * | 2/1977 | Ostojic et al. | 73/864.52 |
| 4,096,734 A | * | 6/1978 | Khayat | 73/23.41 |
| 4,293,379 A | * | 10/1981 | Kelly et al. | 376/159 |
| 4,388,272 A | * | 6/1983 | Gesteland | 422/102 |
| 4,712,434 A | * | 12/1987 | Herwig et al. | 73/864.63 |
| 5,191,211 A | * | 3/1993 | Gorman, Jr. | 250/282 |

(Continued)

FOREIGN PATENT DOCUMENTS

JP 54-126599 A 10/1979

(Continued)

OTHER PUBLICATIONS

"Vapor Pressure", Wikipedia.org, available on the Internet at <http://en.wikipedia.org/wiki/Vapor_pressure>.*

*Primary Examiner*—Hezron Williams
*Assistant Examiner*—David A. Rogers
(74) *Attorney, Agent, or Firm*—Birch Stewart Kolasch & Birch LLP

(57) ABSTRACT

A method and apparatus for ensuring the collecting volatile constituents contained in a solid sample S such as leaf tobacco. In particular, a sample vessel 10 for containing a sample of a solid containing volatile constituents, a gas feeding device 16 for filling the sample vessel with inert gas, a thermostatic chamber 12 for containing the sample vessel and keeping the sample contained in the sample vessel at a predetermined temperature, and a canister 20 designed to be depressurized in advance and selectively connected to the sample vessel are provided. The sample vessel containing the sample S is filled with inert gas, and the sample S is kept at a predetermined temperature. Thereafter, the depressurized canister is connected to the sample vessel, and the constituents evaporating and/or escaping from the sample are collected.

9 Claims, 6 Drawing Sheets

U.S. PATENT DOCUMENTS

| | | | | |
|---|---|---|---|---|
| 5,363,707 A | * | 11/1994 | Augenblick et al. | 73/864.84 |
| 5,433,120 A | * | 7/1995 | Boyd et al. | 73/863.81 |
| 5,437,201 A | * | 8/1995 | Krueger | 73/864.35 |
| 5,463,909 A | * | 11/1995 | Eldridge | 73/864.52 |
| 5,621,180 A | * | 4/1997 | Simon et al. | 73/864.52 |
| 5,700,695 A | * | 12/1997 | Yassinzadeh et al. | 436/180 |
| 5,792,423 A | * | 8/1998 | Markelov | 422/83 |
| 5,863,789 A | * | 1/1999 | Komatsu et al. | 435/262 |
| 5,869,741 A | * | 2/1999 | Scheppers et al. | 73/1.06 |
| 5,932,482 A | * | 8/1999 | Markelov | 436/181 |
| 5,976,468 A | * | 11/1999 | Godec et al. | 422/100 |
| 6,048,404 A | * | 4/2000 | White | 131/275 |
| 6,119,534 A | * | 9/2000 | Dinsmore | 73/864.91 |
| 6,199,436 B1 | * | 3/2001 | Morel et al. | 73/864.52 |
| 6,395,560 B1 | * | 5/2002 | Markelov | 436/181 |
| 6,450,008 B1 | * | 9/2002 | Sunshine et al. | 73/23.34 |
| 6,541,272 B1 | * | 4/2003 | Mitra | 436/178 |
| 2001/0041366 A1 | * | 11/2001 | Lewis et al. | 436/151 |

FOREIGN PATENT DOCUMENTS

| | | |
|---|---|---|
| JP | 3-170838 A | 7/1991 |
| JP | 11-142385 A | 5/1999 |
| WO | WO99/66305 A1 | 12/1999 |

* cited by examiner

APPARATUS AND METHOD FOR EXTRACTING VOLATILE CONSTITUENTS

This application is a Continuation of copending PCT International Application No. PCT/JP02/00668 filed on Jan. 29, 2002, which was published in JAPANESE and which designated the United States, and on which priority is claimed under 35 U.S.C. § 120, the entire contents of which are hereby incorporated by reference.

TECHNICAL FIELD

The invention relates to an apparatus and method for extracting volatile constituents from a solid, which is suited to extract constituents evaporating from leaf tobacco or the like, for example, in order to analyze an aroma of leaf tobacco.

BACKGROUND ART

For example, analysis of an aroma of leaf tobacco is performed by collecting constituents evaporating from the leaf tobacco (laminae or shreds) and analyzing the collected volatile constituents. Further, if flour or the like has abnormal smell, analysis of the abnormal smell of the flour or the like is performed by collecting constituents evaporating and escaping from the flour or the like and analyzing the collected constituents.

A conventional and common way of collecting volatile constituents from a solid is, for example, as shown in FIG. 10, to put a sample S of leaf tobacco or the like in a hermetic container 1 such as a sample vessel, heat it with a heater 2, and collect constituents G which evaporate from the sample S due to the heating and accumulate in an upper space of the hermetic container 1 (a static method; a head space method). Another conventional and common way is, as shown in FIG. 11, to heat a sample S in a hermetic container 3 with a heater 4, and collect constituents G evaporating from the sample S with a collecting agent 6 provided in a collecting tube 5 while the constituents G are continuously circulated between the hermetic container and the collecting tube 5 (a dynamic method).

However, when constituents G evaporating from a sample S are collected in the above-described manners, the respective amounts of the constituents (quantitative relation between the constituents) change under some conditions about heating of the sample S. For example, when heated, constituents contained in a sample S may be thermally decomposed and produce unexpected secondary products. Further, constituents G which evaporate from the sample S vary in volatility, from a high volatility to a low volatility. For example, pressure of a constituent G which is high in volatility and evaporates from the sample S in the hermetic container 1 earliest (inner pressure) may prevent a constituent G which is low in volatility from evaporating from the sample S and make it difficult to collect the latter constituent G. Thus, it is difficult to ensure the collection of volatile constituents which are different in volatility and then to analyze them accurately.

An object of this invention is to provide a method and apparatus for ensuring the extracting and collecting of volatile constituents contained in a solid sample such as leaf tobacco or flour. It is then an object of this invention to perform an analysis on the collected constituents using either an atmospheric concentration technique or a sensory evaluation, i.e. human sense of smell.

In order to achieve the above object, the invention is characterized in that a sample of a solid containing volatile constituents is put in a hermetic sample vessel (hermetic can) with inert gas, and a canister, depressurized in advance, is selectively connected to the sample vessel so that the sample vessel will be depressurized in a moment and constituents evaporating from the sample will be collected into the canister. Thus, the volatile constituents can be extracted from the sample without heating the sample.

Specifically, an apparatus for extracting volatile constituents according to the present invention comprises a sample vessel for containing a sample containing volatile constituents, a gas feeding device for filling the sample vessel containing the sample with inert gas, a thermostatic chamber for containing the sample vessel and keeping the sample contained in the sample vessel at a predetermined temperature (a temperature at which thermal decomposition does not happen, for example, an ordinary temperature), and a canister as a collecting container capable of being depressurized in advance and selectively connected to the sample vessel for collecting constituents evaporating from the sample contained in the sample vessel.

Desirably, the gas feeding device is designed to fill the sample vessel with inert air to replace atmospheric air in the sample vessel containing the sample by the inert gas. The canister is desirably designed to be depressurized to about $1 \times 10^2$ Pa in advance and selectively connected to the sample vessel to collect constituents evaporating from the sample under depressurization, by sucking the constituents with negative pressure in a canister.

A method of extracting volatile constituents according to the present invention comprises the steps of putting a sample containing volatile constituents in a sample vessel, then filling the sample vessel containing the sample with inert gas and keeping the sample at a predetermined temperature (a temperature at which the volatile constituents do not evaporate through thermal decomposition of the sample, for example, an ordinary temperature), and thereafter selectively connecting a canister depressurized in advance to the sample vessel to thereby collect constituents evaporating from the sample under depressurization, into the canister with the inert gas in a moment.

When volatile constituents of the sample are collected into the canister in the above-described way in particular, not only chemical analysis of the volatile constituents with an atmospheric concentration analyzer but also sensory evaluation of the volatile constituents with a human sense of smell can be performed effectively. Further, the volatile constituents can be evaluated as a whole, analytic-chemically as well as sensory-scientifically, irrespective of when the volatile constituents were collected into the canister.

BEST MODE OF CARRYING OUT THE INVENTION

Referring to the attached drawings, an apparatus and method for extracting volatile constituents according to an embodiment of the invention will be described, using an example in which volatile constituents are extracted from leaf tobacco.

Figure 1:
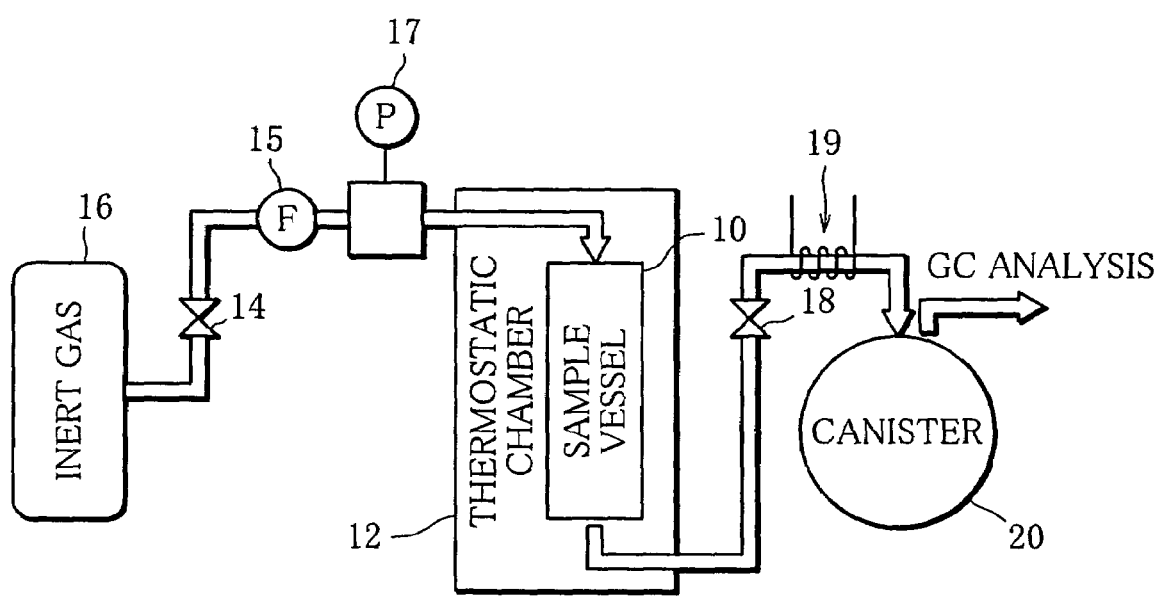
FIG. 1 is a schematic illustration for explaining an apparatus and method for collecting volatile constituents according to an embodiment of the invention.

FIG. 1 is an illustration schematically showing a structure of an apparatus for extracting volatile constituents according to an embodiment of the invention. Reference numeral 10 denotes a sample vessel for containing a sample S of a solid containing volatile constituents such as leaf tobacco, and 12 is a thermostatic chamber for containing the sample vessel 10 and keeping the sample S contained in the sample vessel 10 at a predetermined temperature. To the sample vessel 10 is connected a carrier gas cylinder (bag) 16 with a gas feeding valve 14 between, so that inert gas such as He or $N_2$ can be fed from the carrier gas cylinder (bag) 16 into the sample vessel 10.

The amount of the inert gas fed from the carrier gas cylinder (bag) 16 into the sample vessel 10 is monitored by a flowmeter 15. By filling the sample vessel 10 containing the sample S with inert gas (He, $N_2$ or the like) under open/close control on the gas feeding valve 14, the atmospheric air in the sample vessel 10 is replaced with the inert gas, and the pressure in the sample vessel 10 is set at a desired value. The pressure P of the inert gas fed into the sample vessel 10 is monitored by a pressure gauge 17.

A canister 20 is globular in shape and used as a collecting container is selectively connected to the sample vessel 10 with a collecting valve 18 between. The canister 20 is depressurized to about $1\times10^2$ Pa (1/1000 atm) in advance, and has a capacity of, for example, about 6 liter. The inside of the canister 20 is depressurized in advance. By connecting the depressurized canister 20 to the sample vessel 10 and opening the collecting valve 18, the inside of the sample vessel 10 is depressurized rapidly. Thus, volatile constituents G of the sample S evaporate from the sample S in a moment and are sucked into the canister 20 with negative pressure and collected in the canister 20 with the inert gas.

Reference numeral 19 in FIG. 1 denotes a heater for heating the gas (volatile constituents G of the sample S) collected in the canister 20.

Figure 2:
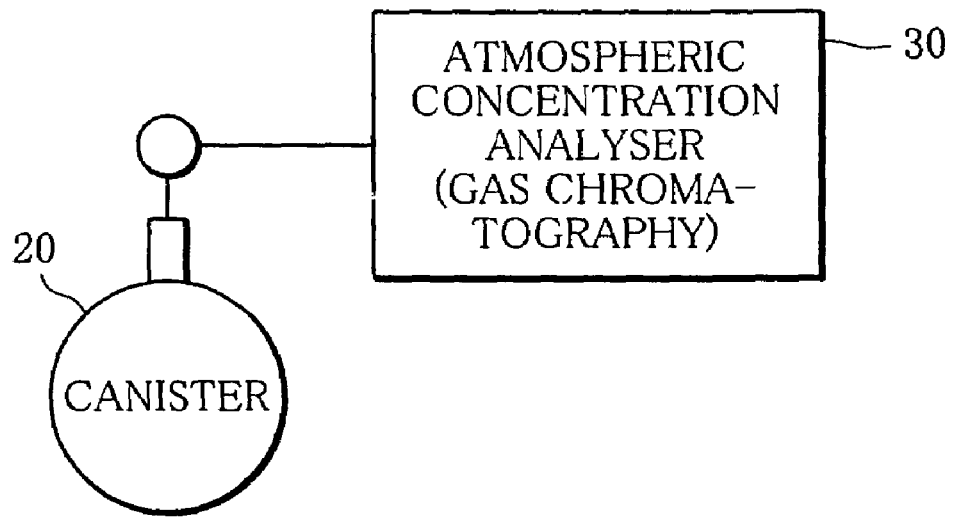
FIG. 2 is an illustration showing how the collected volatile constituents are analyzed with an atmospheric concentration analyzer.
Figure 3:
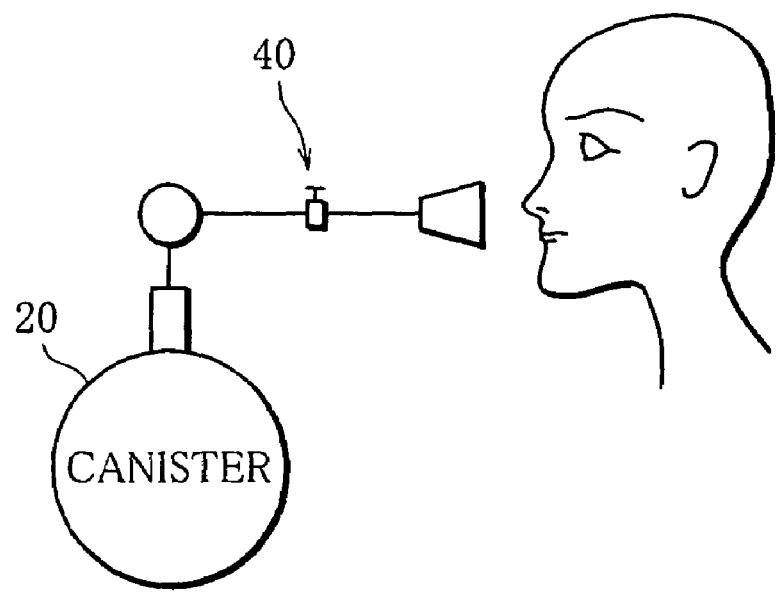
FIG. 3 is an illustration showing how the collected volatile constituents are evaluated with a human sense of smell.

The canister 20, which was selectively connected to the sample vessel 10 and collected constituents G evaporating from the sample S as described above, is then sealed, and then disconnected from the sample vessel 10. Then, as shown in FIG. 2, the canister 20 is fitted to an atmospheric concentration analyzer 30 employing gas chromatography, and the volatile constituents G collected in the canister 20 are analyzed. Alternatively, as shown in FIG. 3, a snifling port 40 with controlled air flow is fitted to the canister 20, and the volatile constituents G collected in the canister 20 are subjected to sensory evaluation by a human sense (sense of smell, etc.)

In the volatile constituent extracting apparatus and method in which constituents G evaporating from a sample S are collected into the canister 20 in the described way, the sample S contained in the sample vessel 10 is not heated. Thus, volatile constituents contained in the sample S is prevented from being thermally decomposed and producing unexpected secondary products. In addition, since the sample vessel 10 is filled with inert gas, constituents G evaporating from the sample S are prevented from combining with constituents of the atmospheric air remaining in the sample vessel which forms a hermetic system, unlike the conventional apparatus and method.

Further, the canister 20 depressurized in advance is selectively connected to the sample vessel 10 which is filled with inert gas and kept at a fixed pressure inside, to thereby decrease the pressure in the sample vessel 10 rapidly. Thus, various volatile constituents G contained in the sample S can evaporate in a moment, and be taken (collected) into the canister 20. As a result, problems with the analysis using the conventional headspace method, specifically, troubles such as balance of collected constituents getting disturbed can be prevented effectively. Further, by controlling the pressure difference between the sample vessel 10 and the canister 20, out of the volatile constituents contained in the sample S, intended volatile constituents can be surely collected, irrespective of degree of volatility, from highly volatile constituents to low volatile constituents.

Another advantage is that since a collecting agent is not used unlike the conventional dynamic method, influence of the kind of a collecting agent on selectivity of constituents can be avoided. Further, since the sample vessel 10 is filled with inert gas as mentioned above, evaporated constituents G escaping from the sample S are prevented from combining with constituents of the atmospheric air remaining in the container which forms a hermetic system. Thus, constituents G evaporating from the sample S can be surely collected.

Figure 4:
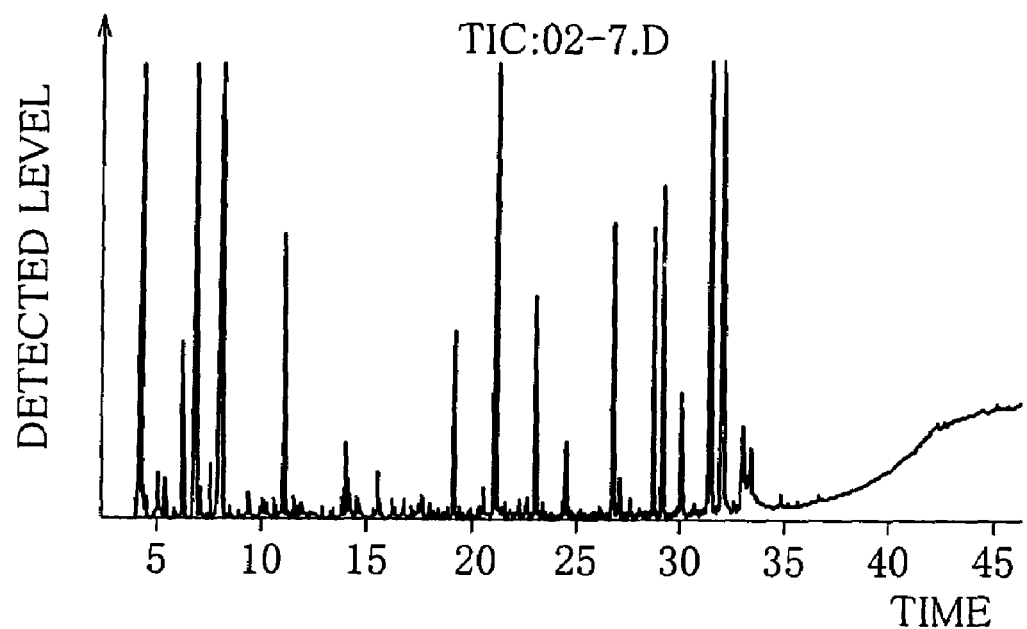
FIG. 4 is a graph showing the result of analysis of volatile constituents collected from leaf tobacco by a collecting method according to the invention.

FIG. 4 shows the result of analysis by gas chromatography of volatile constituents which were collected from leaf tobacco by the volatile constituent extracting method according to the present invention. The analysis was performed as follows: Precisely 2.0 g of leaf tobacco shreds (flue cured type) and filter paper impregnated with 20 μL of 100 ppm isoamyl alcohol as a reference substance were put in a container of 20 mL in capacity (sample vessel 10). Here, the leaf tobacco shreds and the filter paper impregnated with the reference substance together form a test sample S. The test sample S was kept at 40° C. for 10 minutes. After that, 100 mL of evaporated constituents from the sample S was collected using a canister 20 which had been depressurized to about $1\times10^2$ Pa (1/1000 atm). The evaporated constituents collected in the canister 20 were analyzed with a gas chromatography apparatus (atmospheric concentration analyzer).

Figure 5:
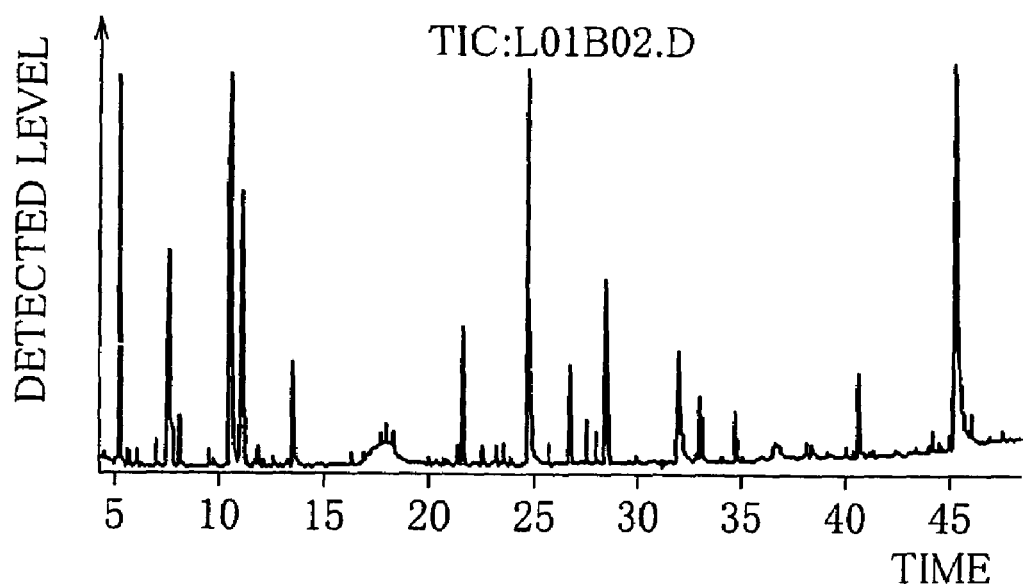
FIG. 5 is a graph showing the result of analysis of volatile constituents collected from leaf tobacco by a conventional static method, for comparison with the result of analysis shown in FIG. 4.

FIG. 5 shows the result of analysis of volatile constituents which were collected from the same test sample by a conventional static method, for comparison with the result of analysis shown in FIG. 4. It is to be noted that the gas chromatography analysis was performed using a gas chromatography analyzer HP6890 (product name) produced by Hewlett-Packard Company, feeding He as carrier gas (in constant float mode), under the condition that the oven temperature was kept at 40° C. for 3 minutes, then raised at the rate of 10° C. per minute, and then kept at 240° C. for 5 minutes.

As clear from comparison between the result shown in FIG. 4 and the result shown in FIG. 5, when volatile constituents of leaf tobacco shreds were collected by the conventional static method, the result of analysis showed that pyrolysates produced due to the heating were contained in the collected constituents. In contrast, regarding the volatile constituent extracting method according to the present invention, it was proved that many volatile constituents can be detected, from highly volatile constituents to low volatile constituents, without being affected by thermal decomposition.

Figure 6:
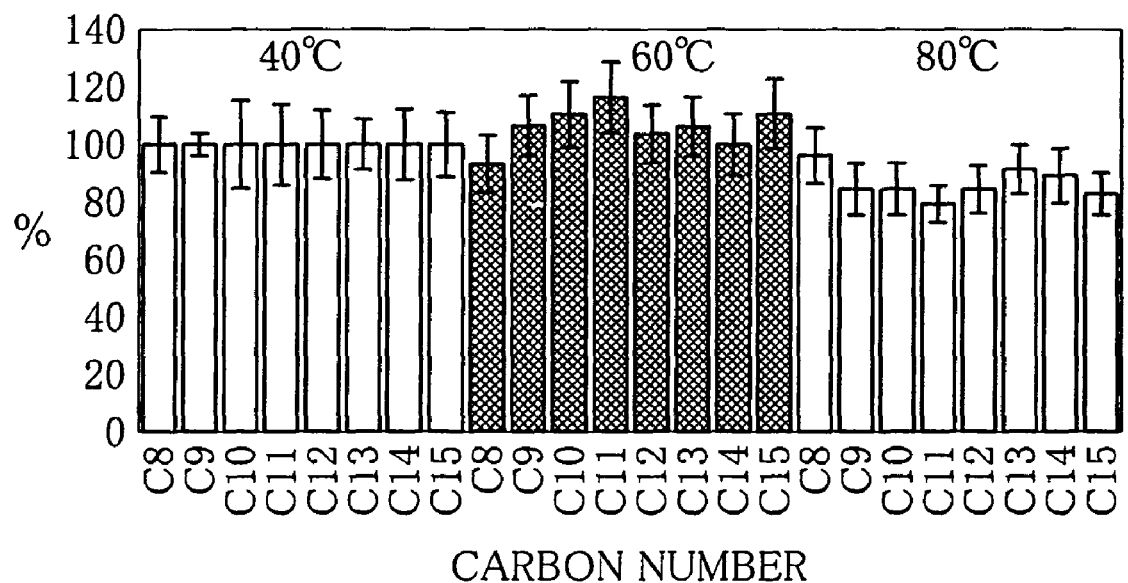
FIG. 6 is a graph showing the result of analysis of volatile constituents collected from a mixture of hydrocarbons by a collecting method according to the invention.

FIG. 6 relates to another test, where precisely 2g of filter paper (product name: ADVANTEC 5C) was put in a container (sample vessel 10) of 20 mL in capacity and got impregnated with 20 µL of a mixture of hydrocarbons as a reference substance (carbon number: C8 to C15). Here, the filter paper impregnated with the reference substance is a test sample S. FIG. 6 shows the result of gas chromatography analysis of volatile constituents collected from this test sample S by the volatile constituent extracting method according to the present invention. When volatile constituents (hydrocarbons) were extracted from the test sample S, the test sample S was kept at 40° C. in one case, at 60° C. for 10 minutes in another case, and at 80° C. for 10 minutes in another case. FIG. 6 shows the volatile constituents collected in those three cases, comparatively.

Figure 7:
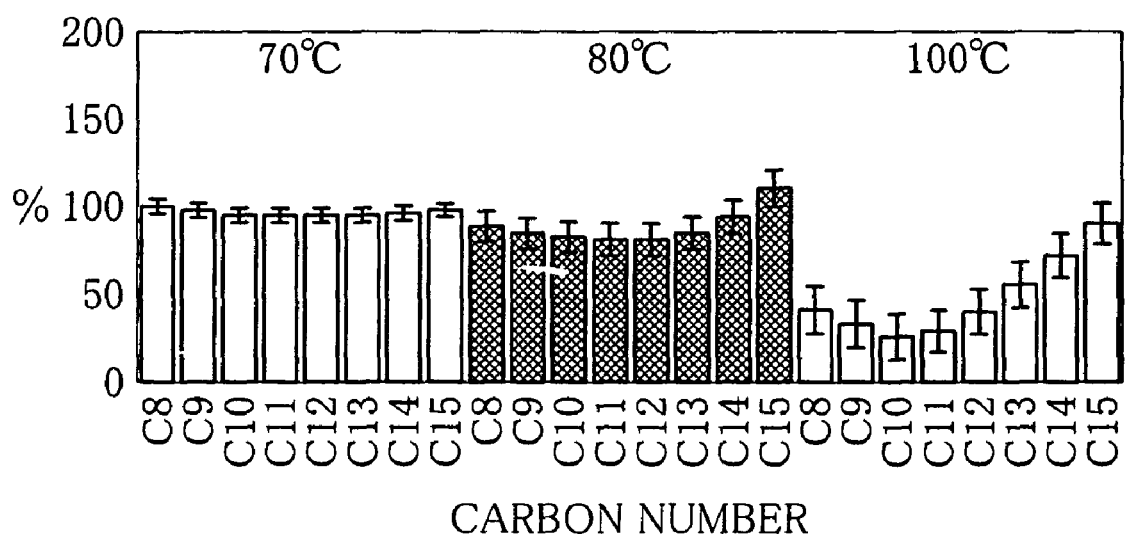
FIG. 7 is a graph showing the result of analysis of volatile constituents collected from a mixture of hydrocarbons by a conventional static method, for comparison with the result of analysis shown in FIG. 6.

FIG. 7 shows the result of analysis of volatile constituents collected from the same test sample S as used in the test of FIG. 6 by a conventional head space method, where the test sample S was heated for 30 minutes to keep it at 70° C. in one case, 80° C. in another case, and 100° C. in another case. It is to be noted that the gas chromatography analysis was performed using a gas chromatography analyzer HP6890 (product name) produced by Hewlett-Packard Company, feeding He as carrier gas (in constant float mode), under the condition that the oven temperature was kept at 40° C. for 3 minutes, then raised at the rate of 10° C. per minute, and then kept at 240° C. for 5 minutes.

As clear from comparison between the result of analysis shown in FIG. 6 and the result of analysis shown in FIG. 7, it was recognized that in the volatile constituent extracting method according to the present invention, even when the test sample was heated, the respective amounts of the collected volatile constituents changed little. This means that the volatile constituent extracting method according to the present invention is little affected by the heating temperature. Also, it was recognized that constituents which do not undergo thermal decomposition are not affected by the heating temperature.

Figure 8:
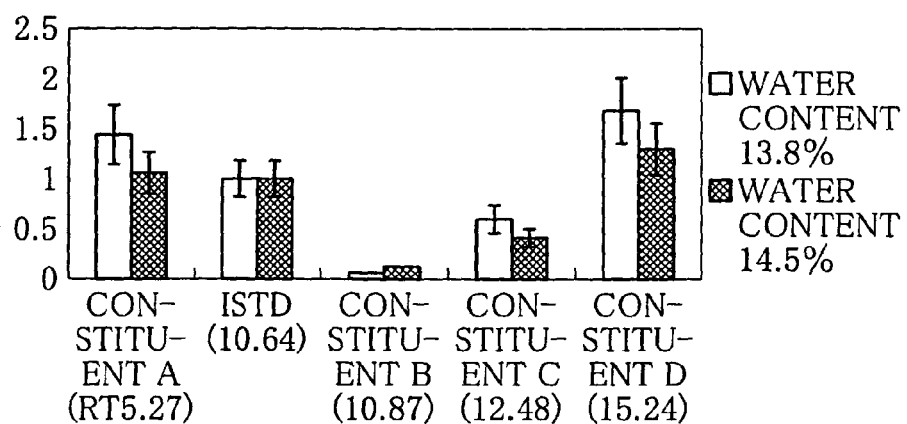
FIG. 8 is a graph showing the result of analysis of volatile constituents which were collected by a collecting method according to the invention from two samples of leaf tobacco different in water content, separately, where the volatile constituents collected from the two samples are shown comparatively.

FIG. 8 relates to anther test, where two test samples S were prepared by putting precisely 2 g of leaf tobacco shreds (flue cured type) having a 13.8% water content and precisely 2 g of leaf tobacco shreds (flue cured type) having a 14.5% water content in a container of 20 mL in capacity (sample vessel 10), separately, each with filter paper impregnated with 5 µL of C10 (0.2% n-dodecanol) as a reference substance. FIG. 8 shows the result of analysis of constituents collected into a canister 20 from each test sample S by the volatile constituent extracting method according to the present invention. Specifically, each test sample contained in the container (sample vessel 10) was kept at 40° C. for 10 minutes, and 1000 mL of constituents evaporating and escaping from each test sample S were collected using a canister 20 depressurized to about $1 \times 10^2$ Pa ($\frac{1}{1000}$ atm). The analysis was performed using a gas chromatography apparatus.

As seen from FIG. 8 which shows the result of analysis of the two test samples having different water contents comparatively, it was proved that the volatile constituent extracting method according to the present invention can surely extract volatile constituents of a sample, hardly being affected by the water content of the sample. In particular, it was recognized that since water contained in a sample was all extracted in a moment by depressurization, it hardly affected the collection of volatile constituents contained in the sample.

Figure 9:
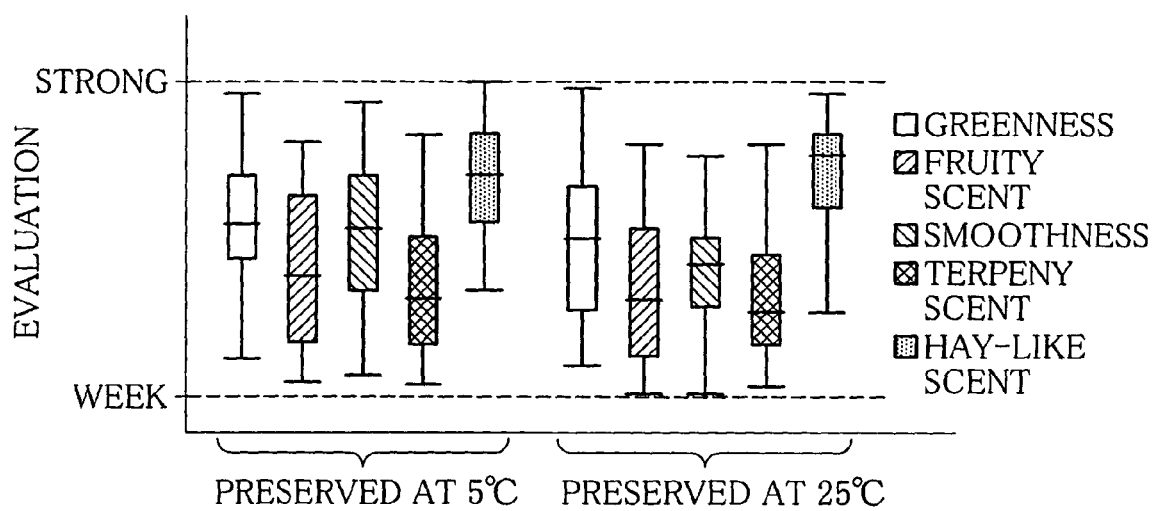
FIG. 9 is a graph showing an example of a result of evaluation of volatile constituents collected in a canister.
Figure 10:
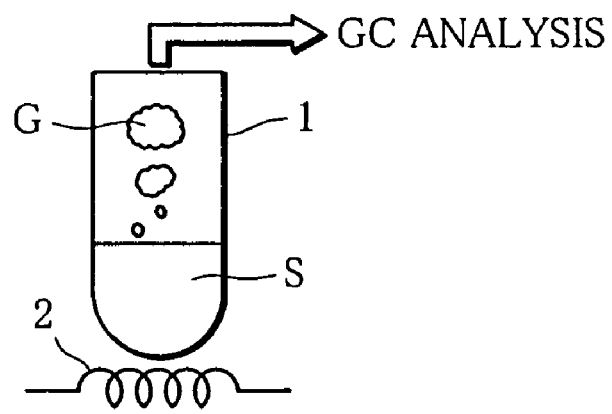
FIG. 10 is an illustration showing how to collect volatile constituents by a conventional static method.
Figure 11:
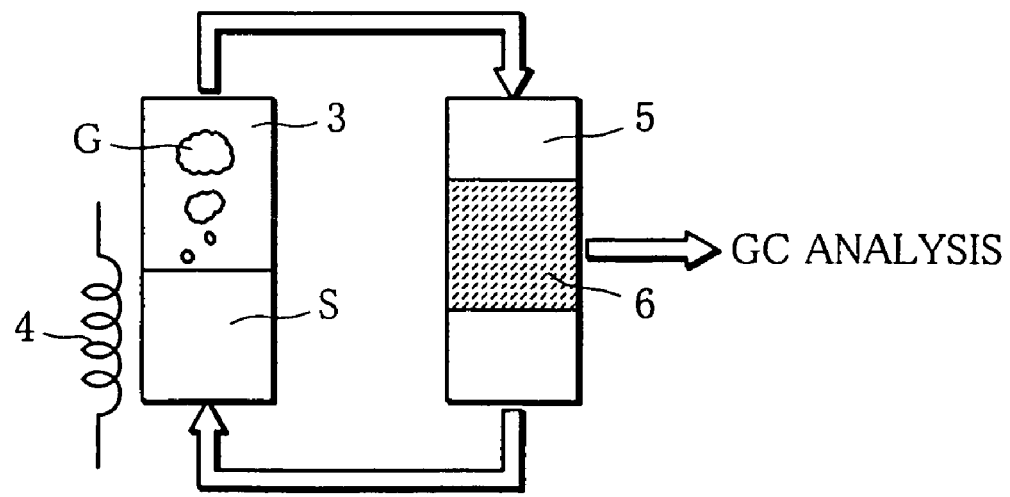
FIG. 11 is an illustration showing how to collect volatile constituents by a conventional dynamic method.

FIG. 9 shows the result of sensory evaluation, where leaf tobacco shreds (flue cured type) which had been preserved at 5° C. for two weeks and leaf tobacco shreds of the same type which had been preserved at 25° C. for two weeks were sensory-evaluated comparatively, in respect of greenness, fruity scent, smoothness, terpeny scent and hay-like scent. Specifically, volatile constituents of the two samples were collected separately in two canisters 20, 20 by the method according to the present invention, and smell of the volatile constituents collected in the two canisters 20, 20 were smelt through snifling port 40, 40 fitted to the canisters 20, 20 and thereby evaluated comparatively.

When the volatile constituents as a whole collected in one canister 20 and those in the other canister 20 are smelt and compared this way, relative differences in the above-mentioned evaluation items can be recognized. Thus, evaluation in respect of the above-mentioned items, which deals with subtle differences and largely relies on human senses (sense of smell, etc.), can be surely performed. It is also possible to use the smell of the volatile constituents collected in one canister 20 as a reference (standard) and evaluate the smell of the volatile constituents collected in the other canister 20 comparatively.

The method of collecting volatile constituents of a sample into a canister 20 this way can be applied to comparative evaluation of volatile constituents collected at different times. Specifically, by collecting volatile constituents in one canister 20 before a sample is subjected to some treatment, and collecting volatile constituents in another canister 20 after the sample is subjected to the treatment, change of volatile constituents of the sample due to the treatment can be analyzed. In other words, when volatile constituents are collected in a canister 20, the collected volatile constituents can be preserved. Thus, off-line analysis of those collected volatile constituents can be performed easily.

The present invention is not limited to the above-described embodiment. In the examples of experiment, volatile constituents were collected, keeping a test sample at 40° C. However, what is essential is to collect volatile constituents, heating a test sample within the range that does not allow unexpected secondary products to be produced due to thermal decomposition. Also when volatile constituents are collected from a test sample, keeping the test sample at an ordinary temperature, like effects can be expected.

Further, while the canister 20 was depressurized to about $1\times10^2$ Pa (1/1000 atm) in advance and then connected to the sample vessel 10, the canister 20 may be depressurized to a greater degree. Conversely, the canister 20 may be depressurized to a smaller degree, for example, to about 10 Pa (1/100 atm), depending on the kind of a sample. The size of the canister 20 is not restricted to any particular one, either. For example, canisters used in the analysis methods denominated TO-14 and TO-15 can be used suitably.

Further, while the above explanation took up the example in which volatile constituents were collected from leaf tobacco shreds, the present invention can also be applied when constituents causing abnormal smell contained in a solid such as flour or confections should be analyzed, or when formaldehyde contained in wall paper should be analyzed. To sum up, the present invention is optimal for collecting volatile constituents evaporating from various kinds of solids to subject them to analysis, and can be carried out with various modifications falling within the scope of the invention.

INDUSTRIAL APPLICABILITY

As explained above, in the present invention, a sample containing volatile constituents is put in a sample vessel with inert gas, and a canister which has been depressurized in advance is selectively connected to the sample vessel. By this, the inside of the sample vessel is depressurized rapidly, which enables the volatile constituents to evaporate from the sample in a moment. The volatile constituents evaporating from the sample are collected into the canister. Thus, the invention can surely collect volatile constituents, from highly volatile constituents to low volatile constituents, without the volatile constituents suffering adverse effects of heating such as thermal decomposition. Further, the invention can surely collect volatile constituents contained in a sample, easily and effectively, irrespective of the water content of the sample, to subject them to analysis. Further, the invention has practically highly beneficial effects such that volatile constituents collected in a canister can be preserved for (analytical-chemical or sensory-scientific) comparative evaluation with other volatile constituents.

The invention claimed is:

1. An apparatus for extracting volatile constituents, comprising:

a sample vessel for containing a sample of a solid containing volatile constituents, a gas feeding device for filling the sample vessel with inert gas, a thermostatic chamber for containing said sample vessel and keeping said sample contained in said sample vessel at a temperature at which said sample is not thermally decomposed, a canister depressurized in advance, and a valve for selectively connecting said canister to said sample vessel contained in said thermostatic chamber and kept at said temperature, thereby depressurizing said sample vessel and collecting constituents evaporating from said sample due to the depressurization, in said canister with said inert gas.

2. The apparatus for extracting volatile constituents according to claim 1, wherein said gas feeding device is designed to replace atmospheric air in said sample vessel with said inert gas, and said canister is depressurized to about $1\times10^2$ Pa in advance to collect all the constituents that evaporate from the sample when said canister is selectively connected to said sample vessel.

3. A method of extracting volatile constituents, comprising the steps of filling a sample vessel containing a sample of a solid containing volatile constituents with inert gas to thereby replace atmospheric air in said sample vessel with said inert gas and keeping said sample at a temperature at which said sample is not thermally decomposed, and thereafter connecting a canister depressurized in advance to said sample vessel in which said sample is kept at the temperature at which said sample is not thermally decomposed, to thereby depressurize said sample vessel and collect constituents evaporating from said sample due to the depressurization, in said canister with said inert gas.

4. The method of extracting volatile constituents according to claim 3, wherein He or $N_2$ is used as said inert gas.

5. A method of extracting volatile constituents from a solid sample containing volatile constituents, comprising the steps of:

(I) providing a sample vessel the interior of which is filled with air;

(II) placing the sample in the sample vessel;

(III) filling the sample vessel with inert gas to thereby displace any air in the sample vessel producing a sample vessel containing the sample and inert gas;

(IV) providing a canister, the interior of which is at sub-atmospheric pressure;

(V) providing a fluid connection between the interior of the canister and the interior of the sample vessel;

whereby the pressure of the interior of the sample vessel is rapidly reduced; whereby the volatile constituents present in the solid are caused to leave the sample and are caused to leave the sample vessel and are caused to collect in the canister.

6. The method of claim 5 wherein the method is practiced at a temperature below which the sample would be thermally decomposed and below which the volatile constituents would be thermally decomposed.

7. The method of claim 5 further comprising the step of:

(VI) analyzing the constituents in the canister.

8. The method of claim 5 wherein the solid sample is a sample of tobacco.

9. An apparatus for extracting volatile constituents from a solid sample containing volatile constituents, said apparatus comprising:

(A) a sample vessel having an interior for holding the solid sample;

(B) means for feeding inert gas to the sample vessel in order to displace any air in the sample vessel and leave the sample vessel substantially completely full of inert gas at atmospheric pressure;

(C) means for maintaining the sample vessel and the solid sample in said the sample vessel at a temperature at which the solid sample is not thermally decomposed;

(D) a canister the interior of which is maintained at sub-atmospheric pressure;

(E) a fluid conduit connecting the interior of the sample vessel to the interior of the canister;

(F) a valve in the conduit for selectively connecting the canister to the sample vessel;

whereby closing the sample vessel when filled with inert gas followed by opening the valve causes: (1) depressurization of the sample vessel, and (2) evaporation of volatile constituents from the solid sample containing volatile constituents, and (3) transfer of the volatile constituents from the solid sample to the canister.

* * * * *